United States Patent [19]

Schoenthal et al.

[11] Patent Number: 4,730,071

[45] Date of Patent: Mar. 8, 1988

[54] PROCESS FOR PREPARING ALUMINOXANES

[75] Inventors: Galeon W. Schoenthal, Houston; Lynn H. Slaugh, Cypress, both of Tex.

[73] Assignee: Shell Oil Company, Houston, Tex.

[21] Appl. No.: 896,689

[22] Filed: Aug. 15, 1986

[51] Int. Cl.$^4$ ................................................ C07F 5/06
[52] U.S. Cl. ...................................... 556/179; 556/175; 556/187; 204/157.62
[58] Field of Search .................... 556/179, 175, 187; 204/157.62

[56] References Cited

U.S. PATENT DOCUMENTS

| | | | |
|---|---|---|---|
| 3,300,458 | 1/1967 | Manyik et al. | 526/352 X |
| 3,954,958 | 5/1976 | Matsui et al. | 556/179 X |
| 4,055,634 | 10/1977 | Brenner et al. | 556/184 X |
| 4,544,762 | 10/1985 | Kaminsky et al. | 556/175 X |

OTHER PUBLICATIONS

The Condensed Chemical Dictionary 4th Edition Reinhold Publ. Corp., N.Y., p. 683 (1950).

*Primary Examiner*—Paul F. Shaver

[57] ABSTRACT

This invention relates to a process for preparing aluminoxanes from trialkyl aluminum compounds and an ultrasonically produced water dispersion.

7 Claims, No Drawings

PROCESS FOR PREPARING ALUMINOXANES

FIELD OF THE INVENTION

This invention relates to a process for preparing aluminoxanes (also referred to as alumoxanes) which are useful in combination with transition metal compounds to prepare polymerization catalysts.

BACKGROUND OF THE INVENTION

Aluminoxanes find use as components in polymerization and oligomerization catalysts. Aluminoxanes have been prepared by reacting a hydrocarbon solution containing trialkyl aluminum with hydrated crystalline salts such as $CuSO_4.5H_2O$ ("Mechanism of Stereochemical Control in Propylene Polymerization with Soluble Group 4B Metallocene/Methylalumoxane Catalysts, *J. Am. Chem. Soc.*, 1984, 106. 6355–6364) and $Al_2SO_4.9-H_2O$ ("Zirconium Catalysts Polymerize Olefins Faster," *Chem. & Eng. News*, July 4, 1983, 29–30 and U.S. Pat. No. 4,544,762, issued Oct. 1, 1985). This technique requires guarding against the possibility of contaminating the aluminoxanes with small amounts of the crystalline salts which can act as poisons when the aluminoxanes are used in polymerization catalysts. In U.S. Pat. No. 3,300,458, issued Jan. 24, 1967 a method is disclosed for preparing aluminoxanes which consists of contacting trialkyl aluminum dissolved in a hydrocarbon solvent with a second hydrocarbon stream which has been saturated with water by contacting the solvent with water in a solvent saturator. In this technique, however, since the amount of water present in the hydrocarbon is small, being limited by the solubility of water in the solvent, relatively large amounts of solvent are required to prepare the aluminoxanes. Manyik et al in "A Soluble Chromium-based Catalyst for Ethylene Trimerization of Polymerization", *Journal of Catalysis*, 47, 197–209, (1977) also discloses the use of water wetted solvent and further discloses the use of the direct addition of water to a dilute solution of trialkyl aluminum. However, the water addition must be done very slowly in order to prepare the aluminoxane rather than aluminum hydroxide.

SUMMARY OF THE INVENTION

This invention relates to a process for preparing aluminoxanes which comprises mixing a first solution of a trialkyl aluminum compound in a liquid, dry, inert hydrocarbon solvent with a second solution of a liquid, inert, hydrocarbon solvent having water ultrasonically dispersed therein. The use of the solution containing ultrasonically dispersed water permits the use of minimal amounts of solvent and allows for a relatively rapid reaction rate to be used over a broad range of temperatures.

DETAILED DESCRIPTION OF THE INVENTION

The aluminoxanes (or alumoxanes) are well-known in the art and are polymeric aluminum compounds which can be represented by the general formula $(R-Al-O)_n$ which is a cyclic compound and $R(R-Al-O)-_nAlR_2$, which is a linear compound. In the general formula, R is a $C_1-C_5$ alkyl group such as, for example, methyl, ethyl, propyl, butyl and pentyl and n is an integer from 1 to about 20. Generally, in the preparation of aluminoxanes from trialkyl aluminum and water, a mixture of the linear and cyclic compounds are obtained.

The aluminoxanes are prepared according to the invention by reacting a $C_1$ to $C_5$ trialkyl aluminum compound ($R_3Al$) in a suitable solvent with water which has been ultrasonically dispersed in a suitable solvent. Illustrative examples of suitable trialkyl aluminum compounds are trimethyl aluminum, triethyl aluminum, tri-isopropyl aluminum, tri-n-propyl aluminum, tri-isobutyl aluminum, tri-n-pentyl aluminum, etc.

The inert solvents that can be used to dissolve the trialkyl aluminum or disperse the water are well known and include the saturated aliphatic compounds such as butane, pentane, hexane, heptane, octane, isoctane, the purified kerosenes, etc.; the cycloaliphatics such as cyclobutane, cyclopentane, cyclohexane, cycloheptane, methylcyclopentane, dimethylcyclopentane, etc.; alkenes and cycloalkenes such as butene, hexene, cyclohexene, octene, etc.; and the aromatic solvents such as benzene, toluene, xylene, etc.; and the like. The major requirements in the selection of a solvent are that it be liquid at the reaction temperature, that it does not reach with the trialkyl aluminum compound or with water or interfere with any subsequent reaction wherein the aluminoxanes are used in polymerization catalysts. The solvents must be oxygen-free. Hydroxyl groups, ether groups, carboxyl groups, keto groups and the like adversely affect preparation of the aluminoxanes.

The aluminoxanes can be produced over a wide range of temperatures, from above the melting point of the solvent to up to the boiling point at the pressure used. Generally, temperatures below about 50° C. are used. Relatively low temperatures can be utilized with the appropriate solvent, say, -100° C. or lower. Pressures are not critical and will typically vary from atmospheric to about 500 psi.

There are numerous pieces of equipment available commercially containing ultrasonic transducers that can be used to ultrasonically disperse the water in the solvent. The ultrasonic baths that are readily available commercially provide suitable means for dispersing the water in the solvent. The amount of water to be dispersed in the organic solvent ranges from just above the limits of solubility of water in the solvent to less than about 5% by weight. There are several alternative methods that can be used to prepare the aluminoxanes of the instant invention. The preferred method is to first ultrasonically disperse the water in suitable solvent, and, while maintaining the ultrasonic power, add the solution of trialkyl aluminum to the water dispersion, allowing the trialkyl aluminum to react with the water to produce the aluminoxane. Alternatively, the ultrasonic power can be shut off prior to adding (with mixing) the trialkyl aluminum solution. The key here is to carry out the reaction prior to the breakup of the water dispersion. The dispersion can be maintained for relatively long periods of time by cooling the dispersion. Very satisfactory results have been obtained by cooling the dispersion to dry ice (-78.5° C.) temperatures. The above reaction should be carried out in an inert, e.g., nitrogen or argon atmosphere.

After reaction, the solvent can be stripped and the aluminoxane isolated as a stable white powder. Preferably, however, the aluminoxane is left dissolved in the solvent, which can then be reacted with suitable transition metal compounds to form polymerization catalysts.

In general, the mole ratio of alkyl aluminum to water will be about 1:1 although variations of this ratio can occur without adversely affecting the aluminoxane product, i.e., the Al/water ratio can vary between about 0.66:1 to about 2:1, preferably about 0.75:1 to about 1.25:1.

The invention will be further described by the following examples which are provided for illustration and are not to be construed as limiting the invention.

EXAMPLE 1

The following represents a typical preparation of an aluminoxane at ambient conditions by the process of the instant invention.

20 Milliliters of dry toluene were placed in a bottle fitted with a nitrogen purge system and the bottle was placed in an ultrasonic bath (Branson). The ultrasonic was started and water (4 millimoles) was added through a hypodermic syringe. After a five minute period of sonification, 4 millimoles (mmoles) of trimethyl aluminum (as a 25 wt% solution of trimethyl aluminum in toluene) was added. Sonification was continued during the reaction to prepare the aluminoxane as evidenced by gas evolution.

EXAMPLE 2

Example 1 was repeated in substantially the same manner except that the ultrasonic bath was maintained at 0° C.

EXAMPLE 3

Example 1 was repeated in substantially the same manner except that the ultrasonic bath was maintained at a temperature of 50° C.

EXAMPLE 4

20 Milliliters of dry toluene were placed in a bottle fitted with a nitrogen purge system and the bottle was placed in the ultrasonic bath. 4 Millimoles of water was injected and sonification was continued for six minutes. The bottle was then removed and chilled in a dry-ice acetone mixture. After chilling, 4 mmoles of trimethyl aluminum (as a 25 wt% solution in toluene) was injected and the reaction to the aluminoxane was allowed to go to completion.

EXAMPLE 5

50 Milliliters of 1-octene were placed in a nitrogen purged bottle which was placed in an ultrasonic bath at ambient temperature. Approximately 4 mmoles of water was injected. After 3 minutes of sonification to disperse the water about 4 mmoles of trimethyl aluminum (as a 25 wt% solution in toluene) was added and the reaction to the aluminoxane was allowed to go to completion.

Embodiment Illustrating Use of Aluminoxanes in Catalyst Preparation

Part A—Oligomerization catalysts according to the teachings of co-pending application Ser. No. 896,700, filed Aug. 15, 1986, now U.S. Pat. No. 4,658,078, issued Apr. 14, 1987, were prepared and tested.

To the aluminoxane solutions of Examples 1-5, 0.5 mmoles of bis(cyclopentadienyl)zirconium dichloride were added with stirring to prepare the catalysts. To examples 1-4 were added 50 ml of 1-octene (Example 5 already continued 1-octene from the aluminoxane preparation). The resultant mixtures were heated to 40° C. for 30 minutes before removing samples for gas chromatographic analysis. Conversions of 1-octene to oligomers are given in the table below.

| Example | % Conversion of 1-Octene |
|---------|--------------------------|
| 1 | 49.8 |
| 2 | 65.0 |
| 3 | 11.7 |
| 4 | 93.5 |
| 5 | 61.9 |

Part B—In this illustrative embodiment various amounts of water was used to prepare the aluminoxane and the results on the dimerization catalysts were measured.

The catalysts were prepared as follows: 20 ml of dry toluene were placed in a bottle fitted with a nitrogen purge system and the bottle was placed in an ultrasonic bath (Branson). The ultrasonic was started and the designated amount of water was added through a hypodermic syringe. After a five minute period of sonification, 4 mmoles of trimethyl aluminum (as a 25 wt% solution in toluene) was added. After the reaction was completed (as evidenced by termination of gas evolution), 50 ml of 1-octene and 0.5 mmole of bis(cyclopentadienyl)zirconium dichloride was added and the mixture was heated to 40° C. After 30 minutes, samples were removed for analysis. The results are shown in the Table below:

| EFFECT OF TRIMETHYL ALUMINUM: WATER RATIO ON 1-OCTENE CONVERSION | | |
|---|---|---|
| Water, mmoles | water/Al | Wt % Conversion of 1-octene |
| 3.0 | 0.75 | 37 |
| 3.2 | 0.8 | 57 |
| 3.6 | 0.9 | 72 |
| 3.9 | 0.975 | 67 |
| 4.0 | 1.0 | 49 |
| 4.2 | 1.05 | 29 |
| 4.7 | 1.175 | 12 |

We claim:

1. A process for preparing aluminoxanes which comprises mixing a first solution of a trialkyl aluminum compound in a liquid, dry, inert hydrocarbon solvent with a second solution of a liquid, inert, hydrocarbon solvent having water ultrasonically dispersed therein wherein the trialkyl aluminum compound and the water react to produce an aluminoxane.

2. The process of claim 1 wherein the alkyl moiety of trialkyl aluminum compound is a $C_1$–$C_5$ alkyl group.

3. The process of claim 2 wherein the alkyl moiety is methyl or ethyl.

4. The process of claim 1 wherein the molar ratio of trialkylaluminum to water ranges from about 0.65:1 to about 2:1.

5. The process of claim 4 wherein the molar ratio ranges from about 0.75:1 to about 1.25:1.

6. The process of claim 5 wherein the molar ratio is about 1:1.

7. The process of claims 1, 2, 3, 4, 5 or 6 carried out at a temperature ranging from about −100° C. to about 50° C.

* * * * *